Figure 1:
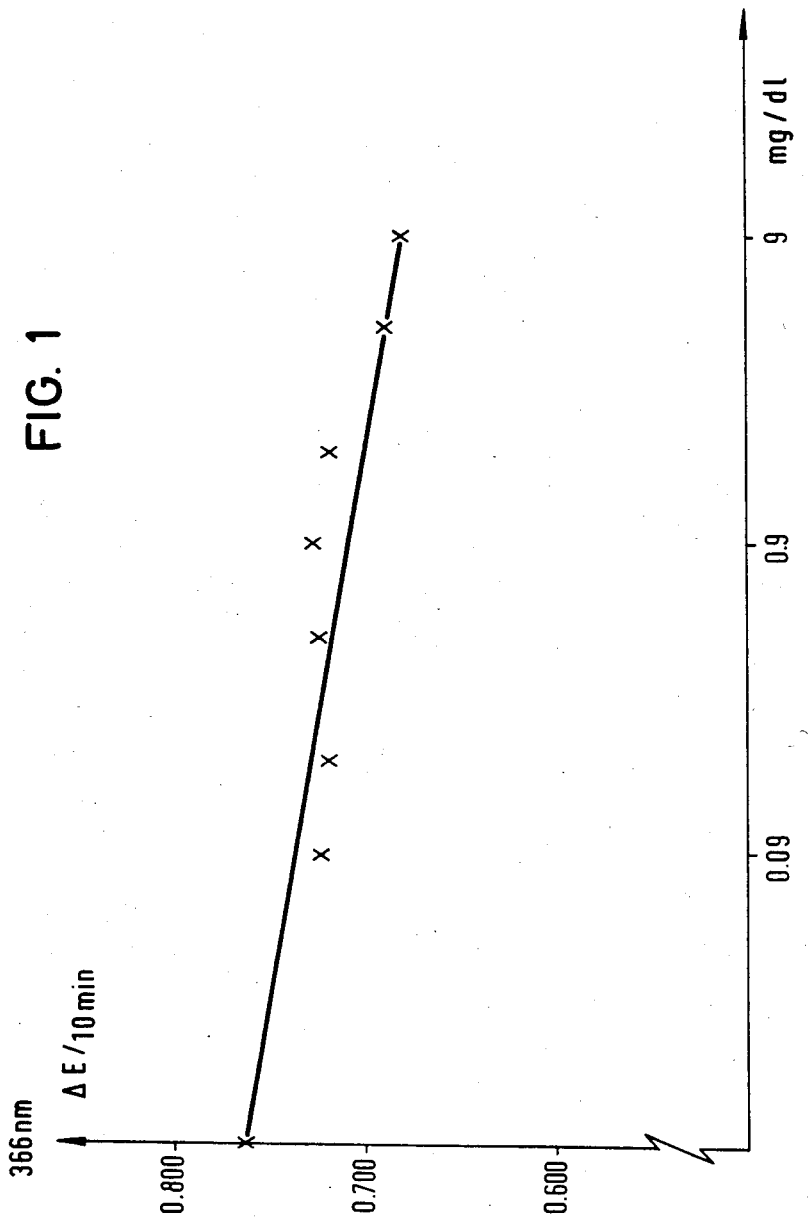

United States Patent [19]

Siedel et al.

[11] Patent Number: 4,578,361
[45] Date of Patent: Mar. 25, 1986

[54] CREATININE ANTIBODY

[75] Inventors: Joachim Siedel, Bernried; Ulrich Neumann, Peissenberg; Joachim Ziegenhorn, Starnberg; Hans-Georg Batz; Helmut Lenz, both of Tutzing; Brigitte Pautz, Herrsching; Winfried Albert, Pähl, all of Fed. Rep. of Germany

[73] Assignee: Boehringer Mannheim GmbH, Mannheim-Waldhof, Fed. Rep. of Germany

[21] Appl. No.: 656,957

[22] Filed: Oct. 2, 1984

Related U.S. Application Data

[62] Division of Ser. No. 412,411, Aug. 27, 1982.

[30] Foreign Application Priority Data

Sep. 2, 1981 [DE] Fed. Rep. of Germany ....... 3134787

[51] Int. Cl.$^4$ ..................... G01N 33/54; A61K 39/00; C07G 7/00
[52] U.S. Cl. ................................. 436/547; 260/112 B; 260/112 R; 424/85
[58] Field of Search ....................... 260/112 B, 112 R; 424/85; 436/547

[56] References Cited

U.S. PATENT DOCUMENTS 4,237,044 12/1980 Würzburg et al. .............. 260/112 B
4,485,177 11/1984 Siedel et al. ....................... 436/547

OTHER PUBLICATIONS

Chem. Abstracts, vol. 93, 200497z, 1980.
Chem. Abstracts, vol. 92, 124433n, 1980.

*Primary Examiner*—Howard E. Schain
*Attorney, Agent, or Firm*—Felfe & Lynch

[57] ABSTRACT

The present invention provides a creatinine antibody and a process for the preparation thereof, wherein a conjugate of creatinine and a material suitable for antiserum formation, which are connected via an aliphatic or araliphatic carboxylic acid as bridge member, is used as immunogen for antiserum formation.

The present invention is also concerned with the use of the above antibody for the immunological determination of creatinine, wherein the antibody is incubated with a creatinine-containing sample solution, reacted with a conjugate of creatinine with a hapten carrier substance, whereby one of the components, antibody and conjugate, is present in the solid phase or in dissolved form and the other component is present in dissolved form and the inhibition of the binding reaction between the antibody and the creatinine conjugate is measured.

Furthermore, the present invention provides a reagent for the immunological determination of creatinine, wherein it contains the above antibody, a conjugate of creatinine with a hapten carrier substance and buffer substance.

16 Claims, 2 Drawing Figures

CREATININE ANTIBODY

This is a divisional application of U.S. Ser. No. 412,411, filed Aug. 27, 1982.

This invention relates to an antibody against creatinine and with a process for the preparation thereof. In additional aspect, the invention relates to the use of the antibody for the determination of creatinine on an immunological basis, and to a reagent for this purpose containing said antibody.

In clinical chemistry, the determination of creatinine is one of the most important methods for the diagnosis of kidney function. In comparison with the determination of urea, it has the decisive advantage that the concentration of creatinine in the serum remains practically uninfluenced by the mode of nutrition and especially by the intake of protein-rich nutriments.

However, in comparison with urea, the concentration of creatinine in the serum in the decisive range (upper limit of the normal values is 1.10 mg./dl. in men and 0.90 mg./dl. in women) is extraordinarily low. Therefore, high requirements must be demanded with regard to the sensitivity and specificity of a creatinine test.

However, because of the importance of the creatinine test as a standard method of investigation in the clinical laboratory, this must, at the same time, be capable of being carried out with the smallest possible expenditure of time and must, in particular, be suitable for use in automatic analysers.

The hitherto most conventional methods for the determination of creatinine depend upon the colour reaction, found by M. Jaffé, of creatinine with picric acid in an alkaline medium. In this case, after acidic deproteinisation of the sample, for example with trichloroacetic acid or picric acid, after the addition of picric acid and rendering alkaline, a red colour develops in the supernatant, which is measured photometrically. However, this per se simple process suffers from a number of important disadvantages.

It has already been shown that the Jaffé reaction is influenced by more than 50 substances which are also chromogenic (see Clin. Chem., 26, 1119–1126/1980) and especially by components which occur naturally in the serum, for example glucose, pyruvate, acetoacetate and acetone, so that it is not specific for creatinine. These "non-creatinine chromogens" are particularly disturbing at low creatinine concentrations ($\leq 1$ mg./dl.), which results in a limitation of the lowermost limit of detection for creatinine ("creatinine-blind" range).

Even small displacements of the pH value of the reaction medium also lead to a change of the colour intensity.

Finally, the use of, in some cases, corrosive and poisonous reagents represents a source of danger in handling. A series of modifications of the Jaffé reaction admittedly improve the precision and the ease of carrying out without, however, completely removing these principle deficiencies.

Another known method converts creatinine, with the addition of o-nitrobenzaldehyde, into methylguanidine, which is then determined by the Sakaguchi reaction. A colour reaction is also known between creatinine and potassium mercury thiocyanate. However, both methods are unsuitable for use in a clinical laboratory.

It is also known to avoid disturbances by non-specific chromogens by a combination of the Jaffe reaction with enzymatic partial reactions. In this case, the coloration obtained by the Jaffe reaction is determined with a serum sample before and after treatment with creatinine amidohydrolase/creatine kinase/ATP and the creatinine content calculated from the difference of the extinctions (see Arch. Pharm. 3, 893–896/1980). This method is admittedly specific but it is difficult to carry out and can also only be automated with difficulty.

Processes for the determination of creatinine are also known in which the ammonia liberated from creatinine by the action of creatinine iminohydrolase is determined, either with ammonia-selective electrodes (see Anal. Chem., 46, 246–249/1976) or fluorimetrically via the utilisation of NADH in a subsequent glutamate dehydrogenase reaction (see Clin. Chim. Acta, 100, 21–23/1980). Because of the possible presence of comparatively large amounts of free ammonia in the sample material, it appears, however, to be questionable whether such measurements can be carried out sufficiently free from disturbances and thus can find acceptance for routine diagnosis.

Recently, a completely enzymatic creatinine test has been described in which creatinine is converted into creatine, the latter reacted with ATP to give creatine phosphate and the ADP thereby formed measured in a coupled reaction with pyruvate kinase and lactate dehydrogenase (LDH) photometrically via the decrease of the NADH content in the reaction solution (see Scand. J. clin. Lab. Invest., suppl., 29, 126/1972).

This method does not require a deproteinisation of the serum sample and is specific for creatinine. However, because of the relatively low measurement signal, even in the case of the use of comparatively large volumes of sample, the sensitivity of the test in the lower creatinine concentration range is limited; in addition, due to the necessity of a sample blank determination, the use of the method in automatic analysers is made very difficult.

Therefore, there is a need for a simple and automatable test for creatinine which, at the same time, is very specific and, for the above-mentioned reasons, is also very sensitive especially in the concentration range of $\leq 1$ mg./dl. of creatinine (the "creatinine blind" range).

Therefore, it is an object of the present invention to overcome the disadvantages of the previously known methods for the determination of creatinine.

According to the present invention, this problem is solved by the provision of a specific antibody against creatinine.

The creatinine antibody according to the present invention is characterised in that it forms a hapten-antibody complex specifically with creatinine.

It is surprising that it is possible to produce an antibody against creatinine since creatinine is a substance which occurs widely in the bodies of all organisms which form antibodies but which itself cannot initiate an antibody formation. Also because of the relatively small molecular size, as well as of the high serum concentration, it was not to have been expected that creatinine, as conjugate with a hapten-carrier substance, could initiate the formation of antibodies which are so specific that, to a noticeable extent, they do not even cross-react with substances, the essential structural characteristics of which are common with those of creatinine, for example creatine and urea, and which, therefore, are suitable for a quantitative method of determination. In this regard, it is also to be pointed out that immunological test methods have admittedly been known for about 40 years and also for a long time there has been a need for an improved method for the determination of creatinine, especially in the low concentration range, without it hitherto having been possible to find such a really specific immunological method for the determination of creatinine.

The preparation of the antibody according to the present invention is characterised in that, as immunogen for the antiserum formation, there is used a conjugate of creatinine and of a material e.g. a protein suitable for antiserum formation which are connected via an aliphatic or araliphatic carboxylic acid as bridge member.

The creatinine conjugate used in the process according to the present invention for the immunisation is prepared by bonding the creatinine to an aliphatic or araliphatic carboxylic acid, whereafter the carboxyl group of the part originating from the carboxylic acid is linked to a hapten carrier substance which can bring about the antiserum formation. Fatty acids with at least 3 carbon atoms and preferably with 4 to 16 carbon atoms, as well as aromatic carboxylic acids containing alkyl side chains, have proved to be especially useful for this purpose. Benzoic acid derivatives with an alkyl radical containing 1 to 4 carbon atoms attached to the aromatic ring have proved to be quite especially suitable. Typical examples thereof include methylbenzoic acid, ethylbenzoic acid and propylbenzoic acid. The oligomers of the araliphatic carboxylic acids, for example methyl benzoate-methylbenzoic acid, can also be used.

The bonding between the creatinine, which is here to be regarded immunologically as a hapten, and the carboxylic acid can be produced by known methods, with the use of activated carboxylic acid derivatives. Use is preferably made of halogenated carboxylic acids, especially of $\omega$-bromocarboxylic acids, in an aqueous alcoholic medium or, in the case of the corresponding halogenated carboxylic acid ester, in an anhydrous medium with subsequent saponification. The best results have been obtained with $\omega$-bromocarboxylic acid esters with subsequent saponification, yields of up to 50% having been achieved. In an aqueous alcoholic medium, the reaction with the creatinine takes place at an elevated temperature and preferably at the boiling point. If carboxylic acid esters are used, then, as solvent, it is preferable to employ polar organic solvents, for example, dimethylformamide, formamide, tetrahydrofuran or the like. The reaction is preferably carried out in the presence of an amine, for example of a mono-, di- or trialkylamine. The saponification of the product can be carried out by gentle warming in an aqueous alkaline medium. Apart from via the nitrogen, the coupling can also take place via the $CH_2$ group by diazotisation with a p-benzoic acid diazonium salt.

The coupling with the hapten carrier substance preferably takes place in an aqueous organic medium in the presence of an amine and of a chloroformic acid ester. Water/dioxan has proved to be especially preferable as a reaction medium.

The creatinine conjugate thus obtained is used as an immunogen for antiserum formation. For this purpose, it is administered to the selected animal species by known methods. Administration can be, for example, intradermal, intramuscular or subcutaneous. The immunogen is preferably used together with Freund's adjuvant in order to increase the antiserum formation. In the case of sheep, the following immunisation scheme has proved to be well suited:

| day | administration | emulsified with | |
|---|---|---|---|
| | | amount of immunogen | Freund adjuvant |
| 0 | intradermal | 1 mg. | + |
| 7 | intramuscular | 1 mg. | + |
| 14 | subcutaneous | 1 mg. | + |
| 30 | intramuscular | 1 mg. | + |
| 60 | subcutaneous | 1 mg. | + |
| etc. | subcutaneous | 1 mg. | + |

The antiserum so obtained, which contains the antibody according to the present invention, can, after dialysis, in which, inter alia, serum creatinine bound to the antibody from the very beginning is also removed, is used for the creatinine determination. Preferably, however, an enrichment and or purification of the antibody takes place. The protein fraction precipitating out up to 1.8 mole/liter ammonium sulphate is thereby preferably isolated and freed by dialysis from low molecular weight components.

A further fine purification can also take place by immunosorption. In this case, the antibody preparation is passed over carrier-bound creatinine conjugate. The antibody is thereby adsorbed on the creatinine conjugate and, after the washing out of impurities, is again eluted with a creatinine solution. By dialysis against acid or salt solution, the complex formed can again be split and pure antibodies are isolated.

Another appropriate method of purification consists in a dialysis of the 1.8 mmole/liter ammonium sulphate fraction against sodium chloride, the addition of creatinine and subsequent incubation with carrier-bound creatinine. The creatinine-specific antibody complex hereby passes through the column and can thus be separated from antibodies of undesired specificity, for example against spacer or hapten carrier substance.

The present invention is also concerned with the use of the new antibody for the determination of creatinine. This use depends upon the fact that the binding reaction between a creatinine conjugate and the antibody which is directed against a creatinine conjugate with either the same or preferably with another hapten carrier substance, is inhibited by creatinine in a concentration-dependent manner. The antibodies can, for example, be used in the form of antiserum or of the immunoglobulin fraction obtained therefrom, which has previously been freed from adhering serum creatinine by an appropriate pre-treatment, for example dialysis against dilute propionic acid or hydrochloric acid (see R. K. Hindawi et al., J. Immunol. Methods, 37, 57–70/1980).

Therefore, the process according to the present invention for the immunological determination of creatinine is characterised in that the creatinine antibody is incubated with a creatinine-containing sample solution, thereafter a conjugate of creatinine with a hapten carrier substance is added thereto, whereby one of the two components, antibody or conjugate, is present in solid or dissolved form and the other component is present in dissolved form and the inhibition of the binding reaction between the antibodies and the creatinine conjugated is measured.

The creatinine conjugate used for obtaining the antibody and for the determination of the binding reaction can be different but, alternatively, can also contain the same hapten carrier substance, for example serum albumin, whereby, in the latter case, cross-reactions against the hapten carrier substance in the test can thereby be selectively prevented in that to the antibody fraction, before determination of the actually interesting binding reaction with the hapten, there is added the hapten carrier substance in the concentration necessary for the precipitation of the antibody directed against the hapten carrier substance, whereby, in the case of carrying out the test via a determination of the turbidity formation (TINIA or NINIA), the precipitates initially formed by the cross-reaction of the creatinine conjugate antibody with the hapten carrier substance are removed, for example by centrifuging or filtration.

The binding inhibition between antibody and creatinine conjugate is the stronger, the more creatinine has been added to the antibody before the mixing with the creatinine conjugate. The inhibiting effect is already strongly marked in a concentration range of the creatinine in the sample solution to be measured of below 1 mg./dl., i.e. the range in which the usefulness of the previously preferably employed and known methods for the determination of creatinine is already very limited.

In the literature, numerous cases have admittedly already been described in which a hapten itself acts as an inhibitor in the case of an immunological binding reaction between an associated hapten conjugate and the antiserum directed against it and this property is also utilised for the quantitative determination of the free hapten by means of various test processes (for example RIA, EMIT, ELISA, TINIA and NINIA). However, in the literature there has hitherto only been described the obtaining of antibodies against low molecular weight substances, such as hormones, which occur in the body of the immunised animal only in very small amounts ($10^{-9}$ to $10^{-12}$ mole/liter; cf. also R. K. Hindawi et al., J. Immunolog. Methods, 37, 57–70/1980.

As hapten carrier substances, use can be made of the materials known for this purpose in immunology. Examples thereof are, in principle, all foreign proteins which do not occur in the host animal which is used for the antibody formation, for example serum albumins of various origin, as well as keyhole lymphocyanine, (lipo)polysaccharides, agarose, polylysine and active charcoal. Examples of other known carrier substances for haptens are mentioned in "Handbook of Experimental Immunology", pub. Blackwell Scientific Publications, 3rd edition (1978) pp. 1–11, which also describes suitable known methods for linking carrier substances to haptens. Preferred hapten carrier substances include serum albumins of various origin, for example bovine serum albumin, human serum albumin and the like and edestin.

By the expression antibody, in the scope of the present invention there are to be understood not only purified antibodies but also antisera, immunoglobulin fractions obtained from the latter, as well as antibody fragments, such as $F(ab)_2$, Fab and Fv fragments.

For the antibody formation, there can generally be used all antibody-forming living creatures, sheep being preferably used. Monoclonal antibodies, such as can be obtained from cell cultures, can also be considered (immunological scheme see enclosure).

The inhibiting action of the creatinine on the binding reaction between the creatinine conjugate and the antibodies can be measured directly according to known immunological methods. As examples there may be mentioned the methods using marked antibodies or antigens, such as RIA or EIA, the latter with the ELISA or EMIT embodiments, the turbidimetric measurement of the inhibition of the immune precipitation between conjugate and antibody (TINIA principle) or the corresponding nephelometric methods (NINIA principle) and the like. Furthermore, there can be used agglutination inhibition tests (PACIA=particle counting immuno-assay) and complement binding reactions. These methods are all well known and do not need to be described here in detail. Merely by way of example, for the EIA embodiment, reference is made to Clin. Chim. Acta, 81, 1–36/1977 and J. Clin. Chem. Clin. Biochem., 18, 197–208/1980.

In the case of enzyme labeling, there can be mentioned the enzymes successfully used for this purpose, for example $\beta$-galactosidase, peroxidase, alkaline phosphatase, glucose oxidase, glucose-6-phosphate dehydrogenase and luciferase. In the case of coenzyme labeling there can be succesfully used e.g. NAD(H) or NADP(H). Not only the antibody but also the hapten can be labeled.

A preferred method amongst the above-mentioned methods consists in that the inhibition of the binding reaction is determined by turbidimetric or nephelometric measurement of the immune precipitation in a predetermined time interval.

Another preferred method consists in that the inhibition of the binding reaction is determined by back titration of non-bound hapten carrier substance-creatinine conjugate with labeled antibodies, especially preferably with enzyme-labeled antibodies, and measurement of the bound or unbound portion of the labeled substance. Suitable for this purpose are, for example, the labeling with radio-active substances (RIA), with enzymes or coenzymes (EIA), fluorescence (FIA) and spin labeling (cf. Nature New Biology, 236, 93–94/1972). As labeled antibodies, there can also be used labeled. antiantibodies (double antibody method).

The present invention also provides a reagent for the immunological determination of creatinine, which contains creatinine antibody, a conjugate of creatinine with a hapten carrier substance and buffer substance.

The reagent according to the present invention preferably also contains a substance which promotes immune precipitation. Especially preferred for this purpose is polyethylene glycol, alone or possibly together with a surface-active substance. The polyethylene glycol used can be one with a molecular weight of from 200 to 20,000, a molecular weight of $6000\pm2000$ being preferred. Preferred concentrations for the polyethylene glycol in the reagent are from 0.1 to 8% by volume.

With regard to the antibody component and the label employed, the above statements apply correspondingly to the reagent according to the present invention.

For the turbidimetric method of determination, according to the present invention a reagent is preferred which contains 0.5 to 500 $\mu$g./ml. of conjugate of creatinine and human serum albumin in the molar ratio of creatinine:human serum albumin of 2 to 60, antibody against creatinine in a mole ratio of 0.1 to 10, referred to the conjugate, 0.1 to 8% by weight polyethylene glycol and buffer substance of the ionic strength of from 0.03 to 0.4 (pH 4 to 10).

For the EMIT method, the reagent according to the present invention preferably contains $10^{-4}$ to $10^{-14}$ mole/liter of antibody against creatinine, referred to active receptor sites, $10^{-4}$ to $10^{-14}$ mole/liter creatinine-malate dehydrogenase conjugate, 0.05 to 50 mmole/liter oxalacetic acid, 5 to 200 mmole phosphate buffer (pH 6 to 8.5) and 0.05 to 0.4 mmole/liter NADH.

As buffer substances, in the scope of the present invention there can be used those which are known to be effective in the pH range of from 4 to 10 and preferably of from 6 to 9. The buffer concentration in the dissolved reagent should be from 0.005 to 1.0 mole/liter and preferably from 0.01 to 0.1 mole/liter, the range of from 0.03 to 0.07 mole/liter being especially preferred.

The antibody concentration in the test is preferably from about $10^{-4}$ to $10^{-14}$ mole/liter and more preferably from $10^{-6}$ to $10^{-12}$ mole/liter, whereby mole/liter is here to be understood to mean active receptor sites.

For carrying out the process according to the present invention, the solution to be analysed can be added directly to the reagent. If the creatinine is present in high concentrations, the sample is preferably previously diluted with water.

In general, the determination can be carried out at a temperature of from 10° to 50° C. and preferably of from 15° to 40° C.

The preparation of the creatinine conjugate can be carried out by known methods, for example according to the mixed anhydride method described in J. Biol. Chem., 228, 713–727/1957. This also applies to labeling with enzymes.

The following examples are given for the purpose of illustrating the present invention, the abbreviations used therein having the following meanings:
CK: creatine kinase
BSA: bovine serum albumin
HSA: human serum albumin
RIA: radio immuno assay
EMIT: enzyme multiplied immunoassay technique
ELISA: enzyme linked immuno sorbent assay
TINIA: turbidity inhibition immuno assay
NINIA: nephelometric inhibition immuno assay
BP: coating buffer
IP: incubation buffer
Tween 20: polyoxyethylene sorbitan monolaurate
DMF: dimethyl formamide
WP: washing buffer
SP: substrate buffer
PNPP-Na: sodium p-nitrophenylphosphate
AT: ambient temperature
AP: alkaline phosphatase
AP-TC: alkaline phosphatase test combination
NAD: nicotinamide-adenine dinucleotide
NADP: nicotinamide-adenine dinucleotide phosphate
TINAQUANT-FN buffer:
    Na,K phosphate: 66 mmole/liter (pH 8.0)
    EDTA: 10 mmole/liter
    Brij-35: 0.4%
    NaN₃: 0.1%
    polyethylene glycol 6000: 2.4%
    Brij-35 polyethylene glycol lauryl ether: 0.4%
    BSA: 0.5%
    HSA: 0.5%

(a) Preparation of the immunogen 1. p-(N-creatininyl)-methylbenzoic acid.

11.3 g. (100 mmole) Creatinine and 21.5 g. (100 mmole) p-bromomethylbenzoic acid are boiled under reflux for 1 hour in 250 ml. of a water-ethanol mixture (1:1 v/v). After cooling, unreacted p-bromoethylbenzoic acid precipitates out. It is filtered off, the filtrate is concentrated to about 100 ml. and then applied to an ion exchanger column (Dowex 148; 200–400 mesh, counter ion formate). The desired product is obtained as pure substance by elution with water; m.p. >250° C.; yield 2.5 g. (9.5% of theory); $R_f$ value (butanol/glacial acetic acid/water 60/15/25 v/v/v)=0.43.

With an $R_f$ value of 0.48, as a further creatinine derivative there is isolated p-(creatinyl)-methylbenzoatemethylbenzoic acid, which can also be used as hapten.

The NMR spectra of the two substances confirm their assumed structures.

2. 3-(N-Creatininyl)-butyric acid.

11.3 g. (100 mmole) Creatinine are suspended in 150 ml. DMF and heated to about 80° to 100° C. To this solution there are slowly added dropwise and simultaneously, while stirring, 17.4 ml. (120 mmole) ethyl bromobutyrate and 16.5 ml. (120 mmole) triethylamine. The reaction mixture is then stirred for 35 hours, the solution thereby becoming almost clear. The solution is filtered and the filtrate obtained is evaporated. The residue is thereafter taken up in water and mixed with active charcoal. After briefly boiling, the active charcoal is filtered off and the filtrate again evaporated. The residue is dried and subsequently recrystallised from isopropanol. The yield of desired product is 10.5 g. (35% of theory); m.p. 176°–178° C.; $R_f$=0.75 (propanol/ammonia/water=5:3:1 v/v/v).

The product is thereby obtained as the hydrobromide. The ester is immediately saponified by dissolving it in water and to this solution a 1N aqueous solution of sodium hydroxide is added dropwise at 40° to 50° C., while maintaining the pH value constant at 10. When no further decrease of the pH value occurs, the reaction mixture is neutralised with 1N hydrochloric acid. The solution is then evaporated to dryness and the residue is taken up in acetone. Insoluble material is removed by filtration and the filtrate is again evaporated. The residue is recrystallised from isopropanol. The product is obtained in the form of a hydrochloride. Yield 5.1 g. (65% of theory); $R_f$=0.66 (methanol/chloroform 1:1 v/v).

3. Coupling of creatininyl-3-butyric acid to bovine serum albumin.

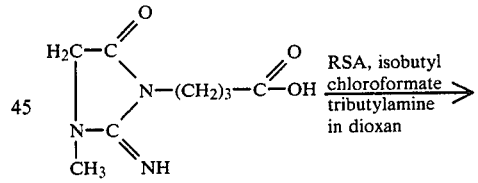

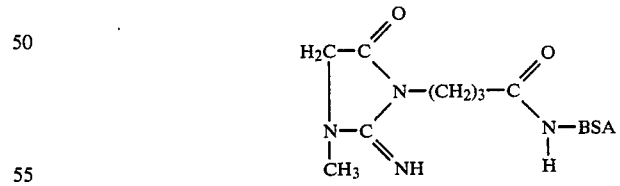

3.6 g. Bovine serum albumin are dissolved in 250 ml. water/dioxan (1:1 v/v) and 5.6 ml. 1N aqueous sodium hydroxide solution are added thereto, solution thereby taking place. The mixture is subsequently cooled to 4° C. To this solution is added dropwise a solution of 1.7 g. creatininylbutyric acid, 1.7 ml. tributylamine and 0.95 ml. isobutyl chloroformate in 60 ml. dioxan and 3 ml. DMF. The reaction mixture is stirred for 24 hours at 4° C., then dialysed against desalinated, flowing water for 36 hours, whereafter the solution is lyophilised.

4. The method according to (3) is repeated but with the use of an equimolar amount of the creatininylmethylbenzoic acid obtained according to (1). The corresponding conjugate with methylbenzoic acid as the bridge member between the creatinine and the albumin is thus obtained.

(b) Preparation of the antiserum

The immunisation of the animals used for obtaining the antiserum is carried out as follows:
Animal species: sheep
Immunogen: creatinine-3-p-methylbenzoic acid-BSA (conjugate)
Immunisation scheme:

| | | emulsified with | |
|---|---|---|---|
| day | administration | amount of immunogen | Freund adjuvant |
| 0 | intradermal | 1 mg. | + |
| 7 | intramuscular | 1 mg. | + |
| 14 | subcutaneous | 1 mg. | + |
| 30 | intramuscular | 1 mg. | + |
| 60 | subcutaneous | 1 mg. | + |
| etc. | subcutaneous | 1 mg. | + |

1. Sample bleeding: day 45.

(c) Preparation of the antiserum

Sheep antiserum is mixed at ambient temperature with 1% "Aerosil", stirred for about 2 hours, centrifuged off and the precipitate discarded. Solid ammonium sulphate is added to the supernatant up to 1.8 mole/liter and then stirred for several hours at 4° C. The mixture is centrifuged, the supernatant is discarded and the precipitate is taken up in 75% of the initial volume (50 mmole K-$PO_4$ and 100 mmole/liter NaCl with 0.05% $NaN_3$; pH 7.0), then dialysed for about 24 hours against 0.15 mole/liter NaCl and subsequently centrifuged, if necessary. The solution can be further treated as follows:

(a) Dialysis against 3 mmole/liter HCl for about 8 to 10 hours with an intermediate change of the dialysis solution (1:100 volume ratio) and the precipitate is centrifuged off and discarded. Dialysis of the solution against 10 mmole/liter $PO_4$ and 150 mmole/liter NaCl for <12 hours (volume ratio 1:100). The precipitate is centrifuged off.

Alternatively:

(b) dialysis against 1 mole/liter propionic acid/liter, period >2 hours, then against 1 mmole/liter HCl (volume ratio 1:100), period >2 hours, neutralisation with sodium bicarbonate. The precipitate is centrifuged off and discarded.

EXAMPLE 1

TINIA principle (a) Reagents

Use is made of the conjugate of creatinine [3-p-methylbenzoic acid], prepared according to Example A, with edestine and bovine serum albumin.

The antiserum obtained according to Example b is dialysed against 1 mole/liter propionic acid and then against 1 mmole/liter hydrochloric acid and thereafter neutralised with sodium bicarbonate. Alternatively, it can be dialysed against 3 mmole hydrochlorid acid/liter and then against a mixture of 10 mmole/liter phosphate buffer and 150 mmole/liter NaCl (pH 7). The precipitate is centrifuged off.

The antiserum dilution takes place with TINA-QUANT-FN buffer (15 minutes after the dilution, the precipitate is possibly again centrifuged off).

Creatinine solution: concentrations of 0.2 to 100 mg./dl.

TINAQUANT-FN buffer (b) Test batch

Into cuvettes (d=1 cm.) each containing 1 ml. amounts of anti-BSA-creatinine antiserum or edestin-creatinine antiserum from sheep (1:5 to 1:50 dilution with TINAQUANT-FN buffer) there are pipetted 100 μl. of creatinine solutions of different concentrations or 100 μl. buffer (for the blank) and then incubated at 25° C. for 5 to 15 minutes.

Then, in each case, 20 μl. of a solution of 1 to 3 mg. HSA- or BSA-creatinine conjugate/ml. TINAQUANT buffer are admixed therewith and the increase of the turbidity measured photometrically at 366 nm after the addition of the HSA-creatinine or BSA creatinine conjugate ($E_1$ before the start, $E_2$ 10 minutes after the start). FIG. 1 of the accompanying drawings shows the calibration curve thus determined, in which the extinction difference is plotted against the creatinine concentration.

EXAMPLE 2

ELISA principle (analogously to the process described J. Immunology, 123, 1548-1550/1979)

(a) Reagents employed

1

BP coating buffer
0.2 mole $Na_2CO_3$/liter, pH 9.3-9.5

2

IP incubation buffer
0.05 mole phosphate, pH 7.2
(28.5 ml. $KH_2PO_4$/71.5 ml. $K_2HPO_4$)
0.1 mole NaCl/liter, 5.85 g./liter
1% glycine
0.05% Tween 20
0.02% $NaN_3$

3

WP wash buffer
0.15 mole NaCl/liter. 8.76 g./liter
0.05% Tween 20
0.02% $NaN_3$

4

SP substrate buffer
AP test
1 table./76 ml. buffer or
17 mg. PNPP-$Na_2$/10 ml. buffer from 123 854

(b) Test batch

Microtitre plates are coated with 200 μl. creatinine-HSA conjugate (50 μg./ml. BP and for the blank 200 μl HSA solution (50 μg/ml BP)) and incubated at ambient temperature for about 16 hours and then aspirated. 300 μl. IP are then added, incubated, again aspirated thereafter 300 μl. WP are added thereto and again aspirated. Subsequently, there takes place the loading with creatinine antiserum. For this purpose, 1000 μl. antiserum diluted 1:200 to 1:2000 with IP, are incubated with 10 μl. creatinine sample or with 10 μl. IP (for the blank) for 30 minutes at ambient temperature, then 200 μl. of the so obtained antiserum dilution are applied to the coated microtitre plates, which are closed for 60 minutes (plastics envelope), left to stand, aspirated, 300 μl. WP added thereto and again aspirated.

Figure 2:
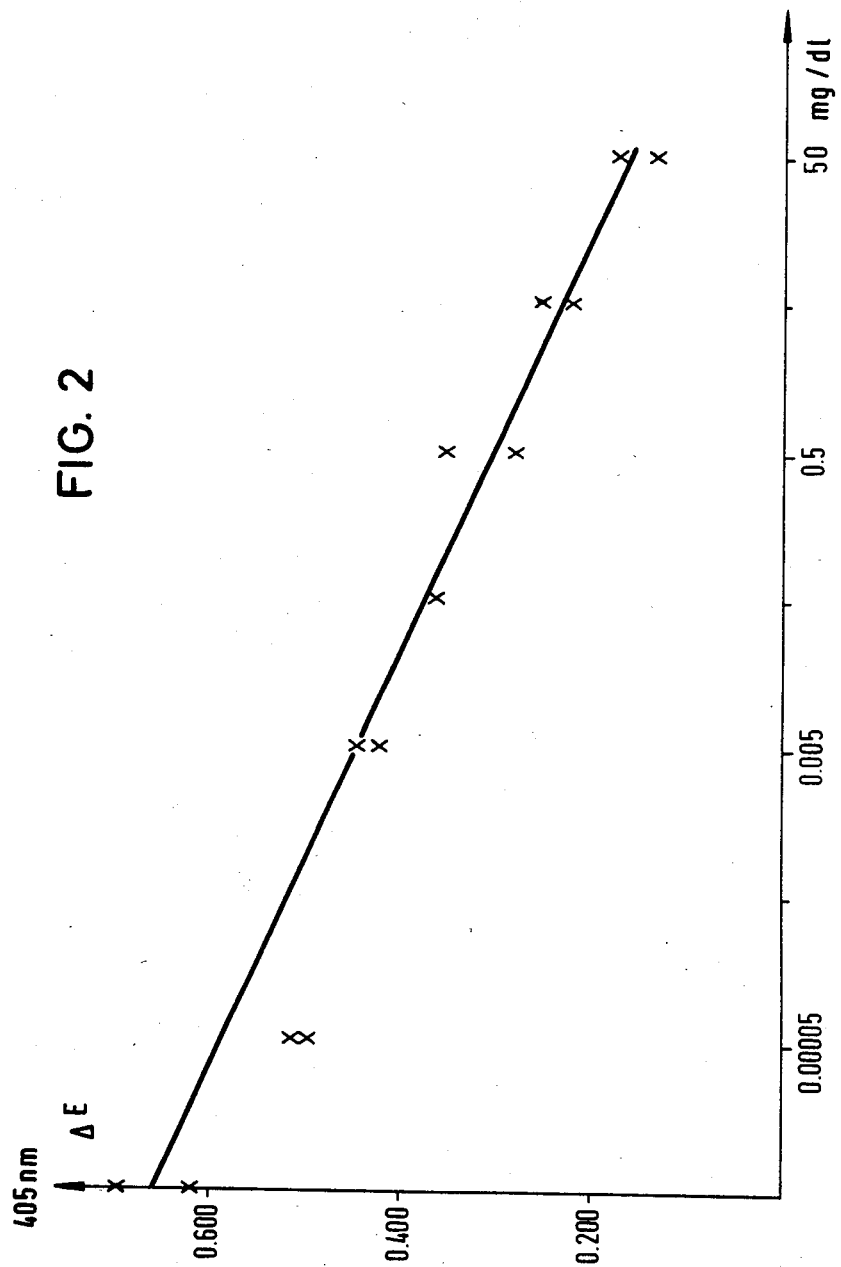

To the conjugate coating, 200 μl. rabbit antisheep IgG-AP containing 150 mU AP/ml. (50 μl. antiantibody labeled with AP in 15 ml. IP) are applied to the treated microtitre plates and maintained for 2 to 3 hours at 37° C., then aspirated and washed twice with 300 μl. WP. For the colour development, 200 μl. substrate buffer (17 mg. PNPP/10 ml. buffer) are added thereto and the mixture incubated for 30 to 60 minutes. The evaluation takes place in that 150 μl. test solution with 500 μl. NaOH, 0.1 mole/liter is measured at 405 nm against a blank. FIG. 2 of the accompanying drawings shows a calibration curve obtained with different creatinine concentrations.

EXAMPLE 3

2.00 ml. 50 mM phosphate buffer (pH 7.5) there are successively admixed:

0.002 ml. sample (or water for the blank)
1.00 ml. $7 \times 10^{-3}$ mole/liter oxalacetic acid in buffer solution (50 mmole/liter phosphate; pH 7.5)
0.01 ml. $4 \times 10^{-7}$ mole/liter creatinine-BSA antiserum or γ-globulin (concentration of binding sites)
0.05 ml. $1 \times 10^{-8}$ mole/liter creatinine-malate dehydrogenase conjugate in buffer solution
0.040 ml. $1.4 \times 10^{-2}$ mole/liter NADH in water.

After the addition of the NADH solution, the enzyme activity (ΔE/min.) is measured spectrophotometrically at 340 nm and at 30° C.

EXAMPLE 4

The procedure described in Example 3 is used but, instead of the oxalacetic acid, there is used the same amount of glucose-6-phosphate and, instead of the creatinine-MDH conjugate there is used a conjugate of glucose-6-phosphate dehydrogenase and instead of the NADH solution and NAD+ solution.

It will be understood that the specification and examples are illustrative but not limitative of the present invention and that other embodiments within the spirit and scope of the invention will suggest themselves to those skilled in the art.

What is claimed is:

1. A method of immunologically determining creatinine which comprises incubating, with a creatinine containing sample a purified creatinine specific antibody which forms a hapten-antibody complex with creatinine, reacting the thus produced mixture with a conjugate of creatinine, said conjugate comprising a hapten carrier substance, at least one of said antibody and said conjugate being present in dissolved form, the second component being present in either dissolved or solid phase form, under conditions favoring binding of said antibody with said creatinine and inhibition of binding of said antibody with said comjugate, measuring the amount of binding between conjugate and antibody and comparing said amount of binding to a standard obtained by binding antibody and conjugate when creatinine is not present, the difference in said amount of binding indicating the amount of creatinine present in said sample.

2. Method as claimed in claim 1, wherein the antibody is used in the form of an antiserum or of an immunoglobulin fraction obtained therefrom.

3. Method as claimed in claim 1, wherein the antibody is used in the form of an antibody fragment.

4. Method as claimed in claim 1, wherein the inhibition of the binding reaction is determined by nephelometric or turbidimetric measurement of the immune precipitation in a predetermined time interval.

5. Method as claimed in claim 1, wherein the inhibition of the binding reaction is determined by back titration of non-bound hapten carrier substance-creatinine conjugate with labeled antibodies and measurement of the bound or non-bound part of the labeled substance.

6. Method as claimed in claim 5, wherein enzyme or coenzyme-labeled antibodies are used.

7. Method as claimed in claim 6, wherein radioactive or fluorescent-labeled antibodies are used.

8. Method as claimed in claim 7, wherein a creatinine conjugate is used, the hapten carrier substance of which does not substantially cross-react with the material used for obtaining the antibody as hapten carrier substance.

9. Method as claimed in claim 8, wherein a creatinine conjugate is used which contains a hapten carrier substance which cross-reacts with the hapten carrier substance used for obtaining the antibody, free hapten carrier substance is mixed with the antibody solution, the precipitate thereby formed is separated off and the supernatant obtained is used as antibody solution in the test.

10. Method as claimed in claim 1, wherein sheep antibody is used.

11. Reagent for immunological determination of creatinine comprising a purified antibody specific to creatinine, a conjugate of creatinine with hapten carrier substance, and a buffer substance.

12. Reagent as claimed in claim 11, additionally containing polyethylene glycol.

13. Reagent as claimed in claim 11, wherein the antibody is present as antiserum, immunoglobulin fraction, antibody fragments or monoclonal antibodies.

14. Reagent as claimed in claim 11, wherein the antibodies are labeled.

15. Reagent as claimed in claim 11, containing 0.5 to 500 μg./ml. conjugate of creatinine and serum albumin in a molar ratio of creatinine:serum albumin of 1:1 to 1:30, antibody:creatinine in the mole ratio of 0.1 to 10, referred to the conjugate, 0.1 to 8% by weight polyethylene glycol and a buffer substance with an ionic strength of 0.03 to 0.4, pH 4 to 10.

16. Reagent as claimed in claim 11, containing $10^{-4}$ to $10^{-14}$ mole/liter antibody against creatinine-hapten carrier conjugate, referred to the active receptor sites, $10^{-4}$ to $10^{-14}$ mole/liter creatinine-malate dehydrogenase conjugate, 0.05 to 50 mmole/liter oxalacetic acid, 5 to 200 mmole/liter phosphate buffer (pH 6 to 8.5) and 0.05 to 0.4 mmole/liter NADH.

* * * * *